United States Patent [19]
Shimoda et al.

[11] Patent Number: 4,879,272
[45] Date of Patent: * Nov. 7, 1989

[54] METHOD AND COMPOSITION FOR PREVENTING THE ADSORPTION OF A MEDICINE

[75] Inventors: Naoto Shimoda; Tsutomu Kawaguchi, both of Saitama, Japan

[73] Assignee: Chugai Seiyaku Kabushiki Kaisha, Tokyo, Japan

[*] Notice: The portion of the term of this patent subsequent to Feb. 21, 2006 has been disclaimed.

[21] Appl. No.: 784,640

[22] Filed: Oct. 4, 1985

[30] Foreign Application Priority Data

Oct. 9, 1984 [JP] Japan ................... 59-210460

[51] Int. Cl.$^4$ ................. A61K 37/02; C07K 15/14
[52] U.S. Cl. ......................... 514/8; 514/776; 514/970; 530/380; 530/395; 424/99; 424/101; 436/8
[58] Field of Search ............... 424/99, 101; 514/8, 514/970, 814, 774, 776; 530/380, 395; 436/8

[56] References Cited

PUBLICATIONS

Horne, cited in *Chem. Abstracts*, vol. 102:163283h, 1985.
Beglinger et al., cited in *Chem. Abstracts* vol. 99:16961u 1983.
Feyerhard et al., cited in *Chem. Abstracts* vol. 95:49281t, 1981.
Hara et al., cited in *Biol. Abstracts* vol. 71(4) Feb. 15, 1981, No. 21876.
Konwalinka et al., cited in *Biol. Abstracts* vol. 78(6), Sep. 15, 1984, No 40961.
Do et al., cited in *Biol. Abstracts* vol. 74(12), Dec. 15, 1982, No. 80937.
Krystal et al., *British Journal of Haemotology;* vol. 58, No. 3, Nov. 1984, 533–546.
Beglinger et al., *Digestive Diseases and Sciences*, vol. 28, No. 4, Apr. 1983.
Horne, *Thrombosis Research* 37; 201–212, 1985.
Krieglstein et al., *Arzneimittel-Forschung*, vol. 22; No. 9, 1972, 1538–1540.
Mizutani et al., *Journal of Pharmaceutical Sciences*, vol. 67, No. 8, Aug. 1978, 1102–1105.

Primary Examiner—Ronald W. Griffin
Assistant Examiner—Jacqueline M. Stone
Attorney, Agent, or Firm—Morgan & Finnegan

[57] ABSTRACT

A method of preventing erythropoietin in an aqueous solution from being adsorbed on the inner surface of the wall of a container by incorporating in the aqueous solution one or more additives, and an erythropoietin composition so formulated as to avoid the adsorption of erythropoietin onto the inner surface of the wall of a container are disclosed.
The additives which are useful in this invention include human serum albumin, bovine serum albumin, lecithin, dextrans, ethylene oxide-propylene oxide copolymers, hydroxypropyl cellulose, methylcellulose, polyoxyethylene hydrogenated castor oils, polyethylene glycols and the like. A 4 Claims, 1 Drawing Sheet

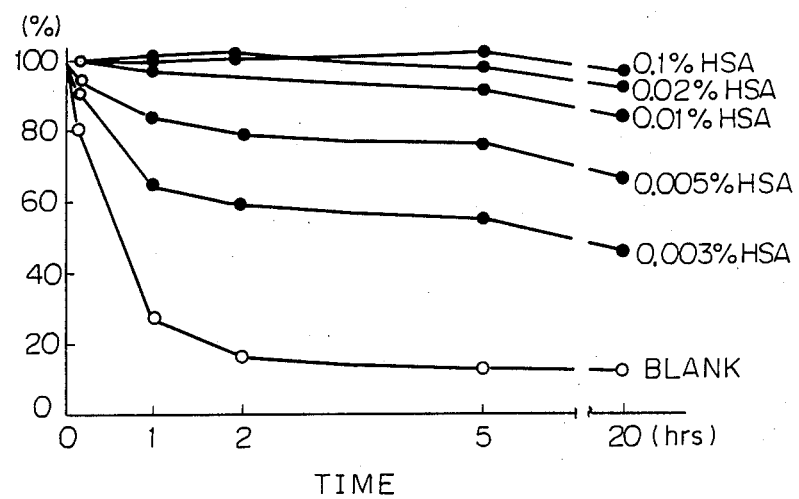

METHOD AND COMPOSITION FOR PREVENTING THE ADSORPTION OF A MEDICINE

BACKGROUND OF THE INVENTION

The present invention relates to a method for preventing erythropoietin in an aqueous solution from being adsorbed on the inner surface of the wall of a container. The invention also relates to an erythropoietin composition so formulated as to avoid the adsorption of erythropoietin onto the inner surface of the wall of a container.

Erythropoietin is a circulating glycoprotein that stimulates the formation of red blood cells and is useful in the treatment or diagnosis of anemia. A single dose of erythropoietin is as small as a few micrograms and this level must be strictly observed. In other words, erythropoietin must be administered in the accurate trace amount in which it is formulated in a dosage form.

However, it has been observed that erythropoietin in an aqueous solution adsorbs on the inner surface of the wall of a glass or plastic container, and the amount that is actually administered is significantly smaller than the amount initially formulated in a dosage form. For example, when an aqueous solution of erythropoietin is charged into a glass or plastic container for transfusion, a considerable amount of erythropoietin is adsorbed on the inner surface of the container wall and this is more likely to occur with lower concentrations of erythropoietin than higher concentrations. Erythropoietin which must be administered in a trace amount has a great chance of adsorption on the inner surface of the wall of a container and because of the smallness of the amount in which it is initially incorporated, the loss of erythropoietin due to adsorption is substantial, causing a significant decrease in the dose that can be actually administered. The necessary and accurate amount of erythropoietin could be dissolved in aqueous solution by taking great care to avoid any adsorption of the erythropoietin on the inner surfaces of the wall of containers and other devices used in the preparation of aqueous erythropoietin solutions. However, when the aqueous solution of erythropoietin is transferred into a glass or plastic syringe for actual administration or if it is injected into a glass or plastic container for mixing with a transfusion solution, a substantial portion of erythropoietin is adsorbed on the inner surface of the wall of the syringe or container, causing serious problems for therapeutic purposes.

Under these circumstances, the present inventors made various studies to develop a method for preventing erythropoietin in aqueous solution from being adsorbed on the inner surface of the wall of a container.

SUMMARY OF THE INVENTION

In accordance with one of its aspects, the present invention provides a method of preventing erythropoietin in aqueous solution from being adsorbed on the inner surface of the wall of a container by incorporating in the aqueous solution one or more additives selected from the group consisting of human serum albumin, bovine serum albumin, lecithin, dextrans, ethylene oxide-propylene oxide copolymers, hydroxypropyl cellulose, methylcellulose, polyoxyethylene hydrogenated castor oils and polyethylene glycols. In accordance with another aspect, the invention provides an erythropoietin-containing composition that prevents erythropoietin from being adsorbed on the inner surface of the wall of a container. The composition capable of achieving this object has one or more of the additives listed above which is mixed with erthropoietin either during the preparation of the composition or just before its administration.

BRIEF DESCRIPTION OF THE DRAWINGS

The FIGURE is a graph showing the relationship between the concentration of human serum albumin, which is one of the additives specified by the present invention, and the percentage of recovery of erythropoietin in the aqueous solutions prepared in Experiments 1 and 2.

DETAILED DESCRIPTION OF THE INVENTION

In accordance with the present invention, the erythropoietin may be obtained by any known method; it may be extracted from the human urine, followed by separation and purification; alternatively, it may be produced in *E. coli*, yeasts or Chinese hamster ovary cells by the genetic engineering technology, and extracted from the culture by a variety of methods, followed by separation and purification. The dosage of erythropoietin varies with the object of a specific diagnosis or treatment, and formulations containing 0.1–50 $\mu$g of erythropoietin per ml may be used. It should however be noted that the present invention is not limited by the erythropoietin content.

As will be shown more specifically by the Experiments given later in this specification, the additive used in the present invention for the purpose of preventing the adsorption of erythropoietin on the inner surface of the wall of a container is at least one member selected from the group consisting of human serum albumin, bovine serum albumin, lecithin, dextrans, ethylene oxide-propylene oxide copolymers, hydroxypropyl cellulose, methylcellulose, polyoxyethylene hydrogenated castor oils and polyethylene glycols. These substances were found to be effective among the many substances that were checked for their ability to prevent the adsorption of erthropoietin on the inner surfaces of the walls of containers. Although the exact mechanism by which these substances prevent erythropoietin from being adsorbed on the inner surfaces of the walls of a containers is not clear, the inventors have found that these substances are specifically selected from attaining the purpose of preventing the adsorption of erythropoietin and that they prevent erythropoietin's adsorption almost completely even if they are used at low concentrations. The additive selected from the group of the substances listed above is desirably incorporated in an amount of at least 0.001% of an aqueous solution in which the erythropoietin-containing composition is dissolved. On the other hand, these substances are desirably used in sufficiently low concentrations so that they will not exhibit pharmacological effects when they are administered to the human body. Therefore, the additive is desirably incorporated in an amount not exceeding 1% of the aqueous erythropoietin solution. It should however be noted that the concentration of the additive is by no means limited to this particular range. As mentioned earlier, the mechanism by which the additive used in the present invention exhibits the ability to prevent erythropoietin's adsorption is not clearly defined, but the effect is obviously the result of its certain action on the inner surface of the wall of the container which contacts the erythropoietin because the same effect is obtained even if the additive is incorporated in the aqueous erythropoietin solution after it is put into a container. This suggests that the minimum necessary amount of the additive in accordance with the present invention is determined not by the content of erythropoietin but by the area of the inner surface of the wall of the container in which the aqueous solution of erythropoietin is put. There is no way to specify the maximum surface area of every container in which erythropoietin is to be put for administration to humans, but as will be shown in Experiments 1 and 2 given later in this specification, the purposes of the present invention can be satisfactorily attained if the additive is incorporated in an amount within the above stated range, i.e., 0.001–1% of an aqueous solution in which the erythropoietin-containing composition is dissolved.

There exist several dosage forms in which the composition of the present invention can be formulated. Erythropoietin and the additive in accordance with the present invention need not be incorporated in the same composition during its preparation. Instead, the two may be prepared as separate entities which are mixed just before administration. Specific examples of the dosage form of the erythropoietin-containing composition are listed below:

(1) a form in which erythropoietin and the additive in accordance with the present invention are incorporated in the same aqueous solution during preparation;

(2) a form which is so designed that separate aqueous solutions of erythropoietin and the additive in accordance with the present invention are mixed just before administration;

(3) a form which is so designed that erythropoietin and the additive in accordance with the present invention are incorporated in the same free-dried powder during its preparation and that the powder is mixed with a separately prepared vehicle for reconstitution just before administration;

(4) a form which is so designed that separate freeze-dried powders of erythropoietin and the additive in accordance with the present invention are dissolved in aqueous solutions which are mixed together just before administration;

(5) a form which is so designed that a freeze-dried powder of erythropoietin and an aqueous solution of the additive in accordance with the present invention are mixed just before administration.

These aqueous solutions and freeze-dried powders may be readily prepared by any of the conventional techniques that are suitable for specific types of preparations. It is within the scope of the invention to add suitable stabilizers or buffers to aqueous solutions, or add buffers to freeze-dried powders, or add suitable excipients for facilitating the freeze-drying operation.

The present invention also provides a method of preventing erythropoietin in aqueous solution from being adsorbed on the inner surface of the wall of a container. In order to prevent erythropoietin's adsorption, the additive that is separately prepared in accordance with the present invention may be added to an erythropoietin-containing transfusion or ampule solution, or alternatively, erythropoietin may be added to a separately prepared transfusion or ampule solution containing the additive in accordance with the present invention. Both methods are included within the concept of the already described invention of an anti-adsorption composition.

The advantages of the present invention are hereunder described with reference to the Experiments.

Experiment 1

Material:

Test samples were prepared by dissolving 0.1%, 0.02%, 0.01%, 0.005% and 0.003% of human serum albumin in PBS solutions. As a control, a pure PBS solution was prepared. Method:

Polyethylene test tubes were filled with 200 μl of the test samples. Ten microliters of PBS solution containing 10 μg (14,000 cpm) of erythropoietin from human urine reductively methylated with $^{14}C$-formaldehyde were put into each of the test tubes, which were then left to stand at room temperature. At 10 minutes, as well as 1, 2, 5 and 20 hours, 20-μl portions were collected from each sample and their radioactivities were measured to determine the percentage of erythropoietin recovery relative to the value for zero minutes.

Results:

The experimental results are shown in the accompanying figure, wherein the BLANK was the pure PBS solution and HSA stands for human serum albumin. The figure clearly shows that human serum albumin, one of the additives specified by the present invention, was an effective agent for the purpose of preventing the adsorption of erythropoietin on the inner surface of the wall of a test tube.

Experiment 2

Additives within the scope of the present invention were dissolved in PBS solutions in the concentrations shown in the Table given below. The samples so prepared were put into polypropylene test tubes, and after addition of erythropoietin solutions as in Experiment 1, the tubes were left to stand at room temperature for 2 hours. The percentages of erythropoietin recovery from the respective samples are shown in the following table.

TABLE

| Additives | Concentration % | Percent recovery of erythropoietin |
|---|---|---|
| Lecithin | 0.01 | 78.6 |
|  | 0.15 | 91.9 |
| Methylcellulose | 0.005 | 80.3 |
|  | 0.025 | 88.2 |
| Polyethylene hydrogenated castor oil, POE (60) | 0.03 | 76.5 |
|  | 0.05 | 92.4 |
| Bovine serum albumin | 0.005 | 81.7 |
|  | 0.02 | 98.8 |
| Dextran 40 | 0.001 | 74.6 |
|  | 0.20 | 93.0 |
| Ethylene oxide-propylene oxide copolymer, F68 | 0.02 | 73.1 |
|  | 0.10 | 87.5 |
| Polyethylene glycol 6000 | 0.05 | 69.2 |
|  | 0.5 | 76.8 |
| None | — | 16.5 |

The above data show that the additives within the scope of the invention were effective in preventing erythropoietin from being adsorbed on the inner surface of the wall of a polypropylene test tube.

The following Examples are provided to further illustrate the present invention.

EXAMPLE 1

An aqueous solution containing 5 g of mannitol, 1 mg or erythropoietin, 100 mg of human serum albumin, 2.154 mg of sodium acetyltryptophanate and 1.33 mg of sodium caprylate in 100 ml was aseptically prepared. One-milliliter portions of this solution were charged into vials and freeze-dried, followed by hermetical sealing of the vials.

EXAMPLE 2

Freeze-dried samples of erythropoietin were prepared as in Example 1 except that 100 mg of human serum albumin was replaced by an equal amount of bovine serum albumin.

EXAMPLE 3

An aqueous solution containing 100 mg of dextran 40, 5 g of sorbitol and 1 mg of erythropoietin in 100 ml was aseptically prepared. One-milliliter portions of the solution were charged into vials and freeze-dried, followed by hermetical sealing.

EXAMPLE 4

An aqueous solution containg 1 mg of erythropoietin, 500 mg of polyethylene glycol 4000, 30 mg of ethylene oxide-propylene oxide copolymer and 800 mg of sodium chloride in 100 ml of 0.05M phosphate buffered solution (pH, 7.0) was aseptically prepared. One-milliliter portions of the solution were charged into ampules, which were sealed by fusing.

EXAMPLE 5

An aqueous solution containing 0.5 mg of erythropoietin, 50 mg of lecithin and 1 g of glycine in 50 ml of 0.05M phosphate buffered solution (pH, 7.0) was aseptically prepared. The solution was distributed among vials in 0.5-ml portions and freeze-dried, followed by hermetical sealing of the vials. A 0.1% aqueous solution of polyoxyethylene hydrogenated castor oil was aseptically prepared and 1-ml portions of the solution were charged into ampules which were sealed by fusion so as to prepare vehicles for reconstitution.

EXAMPLE 6

An aqueous solution containing 0.5 mg of erythropoietin, 1 g of glycine and 1 g of sorbitol in 50 ml of 0.05M phosphate buffered solution (pH, 7.0) was aseptically prepared. The solution was distributed among vials in 0.5-ml portions and freeze-dried, followed by hermetical sealing of the vials. A 0.1% aqueous solution of methylcellulose was aseptically prepared and 1-ml portions of the solution were charged into ampules which were sealed by fusing so as to prepared vehicles for reconstitution.

EXAMPLE 7

An aqueous solution containing 0.5 mg of erythropoietin, 1 g of sorbitol, 25 mg of human serum albumin and 100 mg of hydroxypropyl cellulose in 50 ml of 0.05M phosphate buffered solution (pH, 7.0) was aseptically prepared. The solution was distributed among vials in 0.5-ml portions and freeze-dried, followed by hermetical sealing of the vials.

What is claimed is:

1. A method of preventing erythropoietin in an aqueous solution from being adsorbed on the inner surface of the wall of a container by incorporating in the aqueous solution one or more additives selected from the group consisting of human serum albumin and bovine serum albumin.

2. A method according to claim 1 wherein said one or more additives are incorporated in amounts of 0.001–1% (w/v) of the erythropoietin-containing aqueous solution.

3. An erythropoietin-containing, pharmaceutically-acceptable composition wherein human serum albumin is mixed with erythropoietin either during the preparation of said composition or just before administration thereof.

4. An erythropoietin-containing composition according to claim 3 wherein said bovine serum albumin is incorporated in amounts of 0.001–1% (W/V) of an aqueous solution in which said composition is dissolved.

* * * * *

UNITED STATES PATENT AND TRADEMARK OFFICE
CERTIFICATE OF CORRECTION

PATENT NO. : 4,879,272
DATED : November 7, 1989
INVENTOR(S) : Naoto Shimoda and Tsutomu Kawaguchi It is certified that error appears in the above-identified patent and that said Letters Patent is hereby corrected as shown below:

Claim 4, line 2, "bovine" should read -- human --.

Signed and Sealed this

Thirtieth Day of June, 1992

Attest:

DOUGLAS B. COMER

*Attesting Officer*          *Acting Commissioner of Patents and Trademarks*